US010267771B2

United States Patent
Tissenier et al.

(10) Patent No.: US 10,267,771 B2
(45) Date of Patent: Apr. 23, 2019

(54) METHOD FOR TESTING A STRUCTURAL COMPONENT OF A VEHICLE

(71) Applicants: Airbus Operations SAS, Toulouse (FR); Airbus SAS, Blagnac (FR)

(72) Inventors: Alain Tissenier, Toulouse (FR); Aurelien Rautureau, Blagnac (FR)

(73) Assignees: AIRBUS OPERATIONS SAS, Toulouse (FR); AIRBUS SAS, Blagnac (FR)

( * ) Notice: Subject to any disclaimer, the term of this patent is extended or adjusted under 35 U.S.C. 154(b) by 94 days.

(21) Appl. No.: 15/490,275

(22) Filed: Apr. 18, 2017

(65) Prior Publication Data
US 2017/0307569 A1    Oct. 26, 2017

(30) Foreign Application Priority Data

Apr. 22, 2016 (FR) ..................................... 16 53575
Apr. 22, 2016 (FR) ..................................... 16 53576

(51) Int. Cl.
*G01N 29/48* (2006.01)
*G01N 29/265* (2006.01)
(Continued)

(52) U.S. Cl.
CPC ......... *G01N 29/043* (2013.01); *G01N 29/221* (2013.01); *G01N 29/225* (2013.01);
(Continued)

(58) Field of Classification Search
CPC ... G01N 29/44; G01N 29/04; G01N 2291/101
(Continued)

(56) References Cited

U.S. PATENT DOCUMENTS 4,229,796 A    10/1980  Garrett
4,751,657 A  *  6/1988  Imam ................... G01H 1/003
                                                                  702/35

(Continued)

FOREIGN PATENT DOCUMENTS

FR             2957418          9/2011

OTHER PUBLICATIONS

French Search Report, dated Jan. 10, 2017, priority document FR1653575.
French Search Report, dated Jan. 10, 2017, priority document FR1653576.

*Primary Examiner* — Jacques M Saint Surin
(74) *Attorney, Agent, or Firm* — Greer, Burns & Crain, Ltd.

(57) ABSTRACT

A method for structural component crack testing comprising: a) identifying a structural component hole and inserting a probe thereinto; b) for different emission directions, automatically performing the following: b1) controlling a probe ultrasound beam emission; b2) measuring a probe signal; b3) if the measured signal amplitude is above a predetermined threshold: determining a distance between the probe and a structural component discontinuity point; recording a data set comprising at least the distance between the probe and the discontinuity point, together with a data element corresponding to the probe emission angular direction, c) automatically searching for data sets corresponding to characteristic discontinuity points, and consequently establishing a correspondence between the probe emission angular directions and an angular reference frame linked to the component; d) based on the recorded data sets, automatically determining the discontinuity point positions; e) determining a dimensional characteristic of a crack based on the discontinuity point positions.

11 Claims, 12 Drawing Sheets

(51) Int. Cl.
*G01N 29/22* (2006.01)
*G01N 29/24* (2006.01)
*G01N 29/04* (2006.01)
*G01N 29/44* (2006.01)

(52) U.S. Cl.
CPC ....... *G01N 29/2487* (2013.01); *G01N 29/265* (2013.01); *G01N 29/4436* (2013.01); *G01N 29/48* (2013.01); *G01N 2291/0289* (2013.01); *G01N 2291/044* (2013.01); *G01N 2291/101* (2013.01); *G01N 2291/2694* (2013.01)

(58) Field of Classification Search
USPC .......................................................... 73/632
See application file for complete search history.

(56) References Cited

U.S. PATENT DOCUMENTS

| | | | |
|---|---|---|---|
| 6,098,022 A * | 8/2000 | Sonnichsen | G01M 13/028 702/190 |
| 7,464,596 B2 * | 12/2008 | Bui | G01N 29/043 73/618 |
| 9,103,741 B2 * | 8/2015 | Baik | G01M 5/0016 |
| 2007/0007955 A1 * | 1/2007 | Goldfine | G01N 27/82 324/240 |
| 2009/0229365 A1 | 9/2009 | Bentzel | |
| 2013/0220018 A1 | 8/2013 | Kollgaard et al. | |
| 2015/0355146 A1 * | 12/2015 | Uematsu | G01N 29/28 73/644 |

* cited by examiner

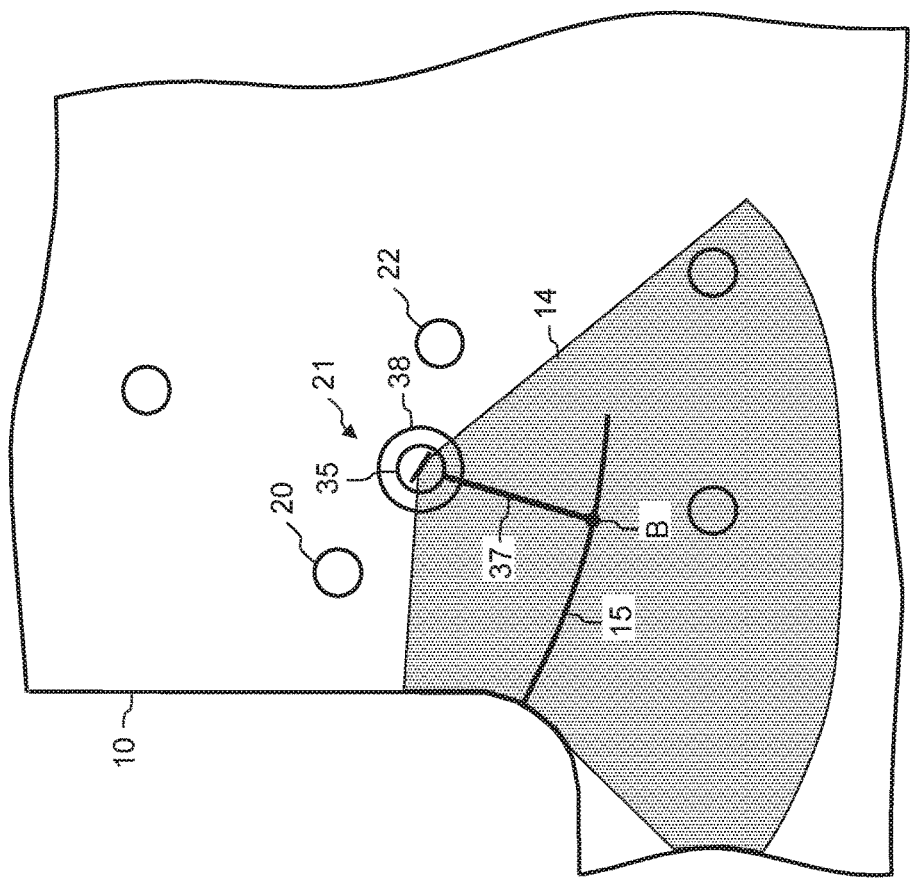
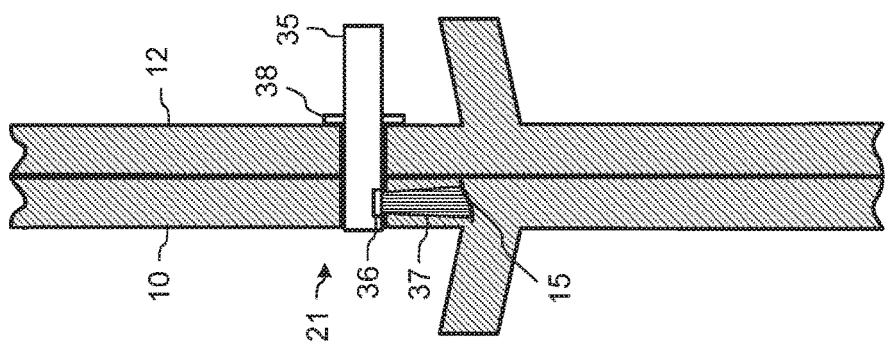

METHOD FOR TESTING A STRUCTURAL COMPONENT OF A VEHICLE

CROSS-REFERENCES TO RELATED APPLICATIONS

This application claims the benefit of the French patent application No. 1653575 filed on Apr. 22, 2017, and the French patent application No. 1653576 filed on Apr. 22, 2017, the entire disclosures of which are incorporated herein by way of reference.

BACKGROUND OF THE INVENTION

The invention relates to the testing of a structural component of a vehicle, more particularly for the purpose of detecting a crack in such a component. Some structural components of a vehicle, such as an aircraft, are regularly subjected to stresses during the use of the vehicle, which may result in cracks in the components. In order to use the vehicle in adequate conditions of safety, these structural components must be tested in periodic test inspections. In these test inspections, operators check whether a structural component has a crack, and, if so, must estimate certain dimensional characteristics of the crack, particularly its length. For some components, the operators may detect a crack by visual inspection or by moving a sensor over the surface of the component. However, other components are more difficult to access, and such a procedure is not feasible for the detection of a possible crack. In particular, a component to be inspected may be assembled with another component, this other component preventing both visual inspection and the movement of a sensor over the component to be inspected. For example, a structural component 10 shown separately in FIG. 1A has a crack 15. This structural component is assembled with another component 12, shown separately in FIG. 2A. These two components have a set of fastening holes such as the hole marked 21 in the figures. These fastening holes may be used to assemble the components by using fastening means such as bolts or rivets. FIG. 3A shows the structural component 10 and the component 12 assembled together. The component 12 prevents an operator from accessing the structural component 10 to inspect the crack 15. FIGS. 1B, 2B, and 3B show the components 10 and/or 12, in sections taken along the line A-A of FIGS. 1A, 2A and 3A respectively. Some structural components are also difficult for an operator to access: in some cases, the operator may touch a component, but finds it difficult to see it while manipulating the component. It would therefore be desirable to improve the methods of testing structural components, in order to facilitate the detection of a crack in a component which is difficult to access and/or is masked by another component.

SUMMARY OF THE INVENTION

An object of the present invention is, notably, to provide a solution to these problems. It relates to a method for crack testing in a structural component of a vehicle. This method is remarkable in that it comprises the following steps:
  a) identifying a hole of circular cross section in the structural component and inserting into the hole a probe comprising at least one ultrasonic transducer, the probe being equipped with a rotation sensor and/or a motor;
  b) moving the probe rotationally in the hole so as to move the direction of emission of an ultrasound beam by the probe, and, for each angular position of the probe among a set of different angular positions of the probe, performing the following sub-steps automatically, by means of a control system:
    b1) controlling the emission of an ultrasound beam into the structural component;
    b2) measuring a signal supplied by the probe, corresponding to an echo of the emitted ultrasound beam;
    b3) if the amplitude of the measured signal is above a predetermined threshold:
    determining a distance between the probe and a point of discontinuity in the structural component, on the basis of the measured signal;
    determining the angular position of the probe;
    recording a data set comprising at least the distance between the probe and the point of discontinuity, together with a data element corresponding to the angular position of the probe,
  c) automatically searching, by means of the control system, among the data sets recorded for the different angular positions of the probe, for data sets corresponding to characteristic points of discontinuity of the structural component, and establishing a correspondence between the angular positions of the probe on the one hand, and an angular reference frame linked to the component on the other hand;
  d) on the basis of the data sets recorded for the different angular positions of the probe, automatically determining, by means of the control system, the positions in the structural component of the points of discontinuity corresponding to the angular positions of the probe for which the amplitude of the measured signal is above the predetermined threshold;
  e) determining at least one dimensional characteristic of a crack in the structural component on the basis of the positions of the points of discontinuity.

This method enables an ultrasound beam to be emitted in the thickness of the structural component from the hole in which the probe is inserted. By moving the probe rotationally in the hole, the direction of emission of the ultrasound beam by the probe may be oriented in a plurality of angular positions. It is thus possible to detect automatically, in the structural component, points of discontinuity corresponding to the crack which is being sought. For each detected point of discontinuity, the recording of the distance determined between the probe and this point, together with the corresponding angular position, enables the position of the point in the structural component to be determined automatically. By identifying characteristic points of discontinuity, a correspondence may be established automatically between the angular positions of the probe and an angular reference frame linked to the component: this makes it unnecessary to reference the position of the probe relative to the component, and thus facilitates the user's work. After determining the positions in the structural component of a set of points corresponding to the crack, it is thus possible to determine at least one dimensional characteristic of the crack.

According to one embodiment, the probe being equipped with a motor, in step b) the rotational movement of the probe in the hole is controlled automatically by the control system.

In a particular embodiment, the rotation sensor being a rotary encoder, in step a) the probe is inserted into the hole until the rotary encoder comes into contact with the structural component or with a component assembled onto the structural component.

According to another particular embodiment, step b) is repeated after step c).

Advantageously, step e) is executed automatically by the control system.

Advantageously, step e) comprises the determination of a length of the crack in the structural component.

According to a particular embodiment, in step a) the probe is inserted into the hole in the structural component through another component adjacent to the structural component.

According to another particular embodiment, steps a), b), c) and d) are repeated for at least two holes in the structural component.

In an advantageous embodiment, the probe being a multi-element ultrasonic probe, step b) is repeated with the ultrasound beam emitted toward a plurality of locations distributed within the thickness of the structural component.

In another advantageous embodiment, the probe being a multi-element ultrasonic probe, steps b1) to b3) are repeated with the ultrasound beam emitted toward a plurality of locations distributed within the thickness of the structural component.

BRIEF DESCRIPTION OF THE DRAWINGS

The invention will be more readily understood from a perusal of the following description and the accompanying figures.

DETAILED DESCRIPTION OF THE PREFERRED EMBODIMENTS

Figure 1A:
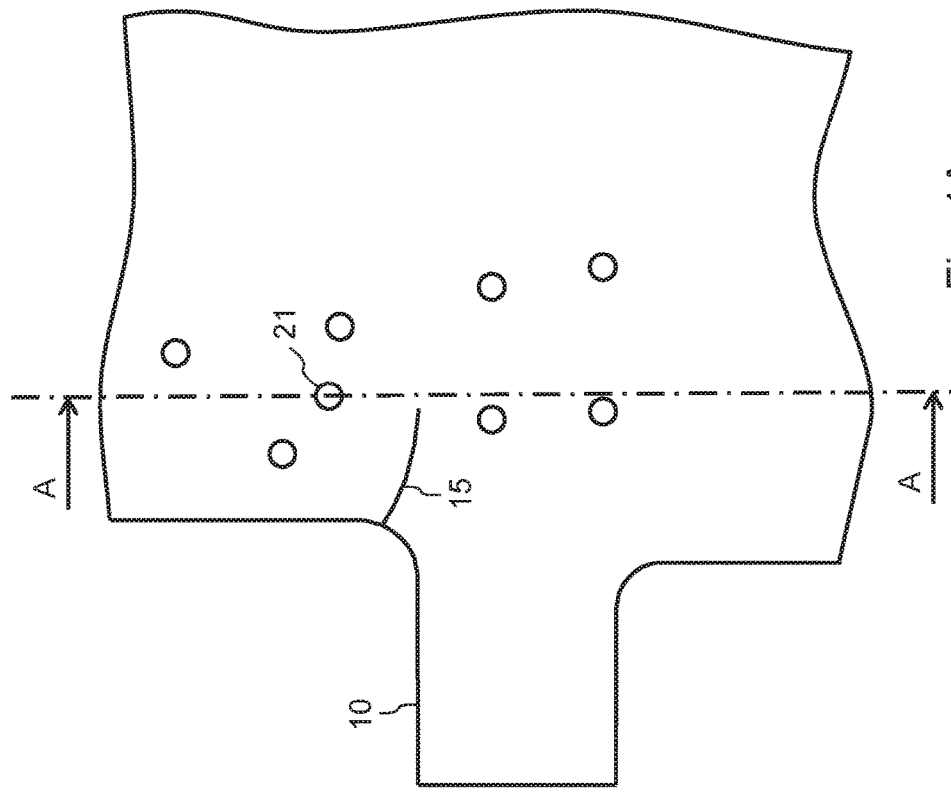
FIGS. 1A, 2A and 3A, already described, represent in a simplified manner a structural component of a vehicle and another component assembled onto this structural component.
Figure 1B:
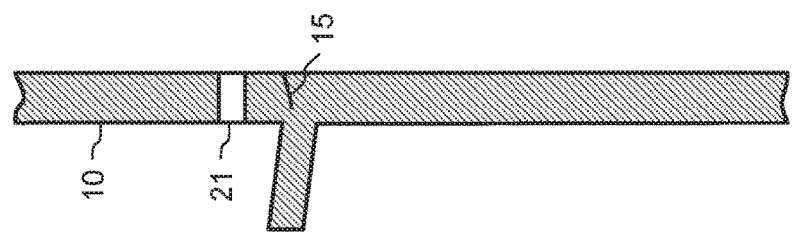
FIGS. 1B, 2B, and 3B, already described, show sections taken along the line A-A of FIGS. 1A, 2A and 3A respectively.
Figure 2A:
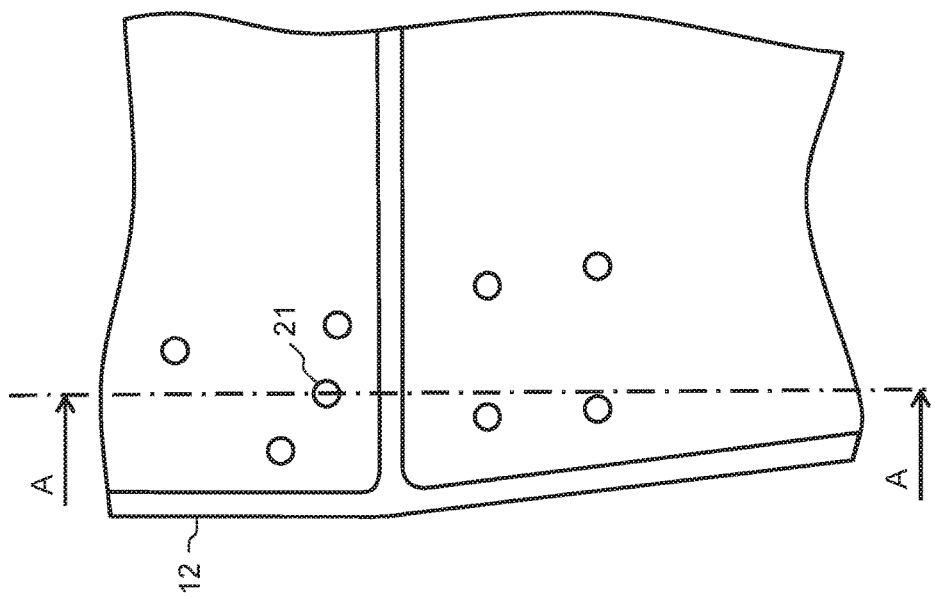
Figure 2B:
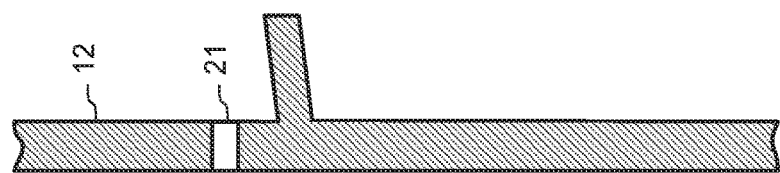
Figure 3A:
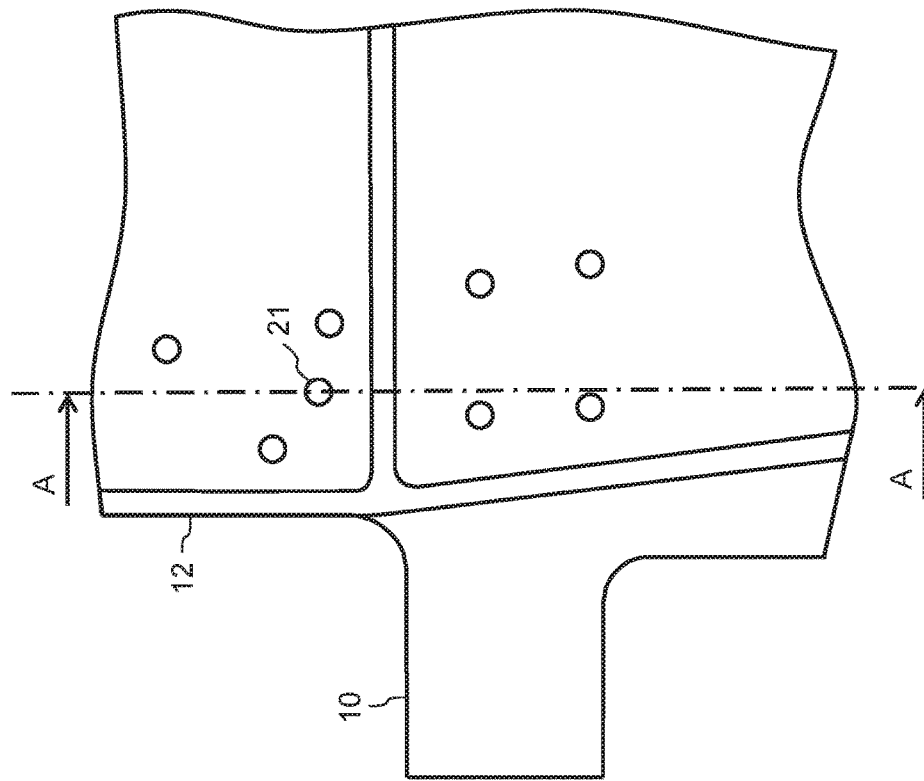
Figure 3B:
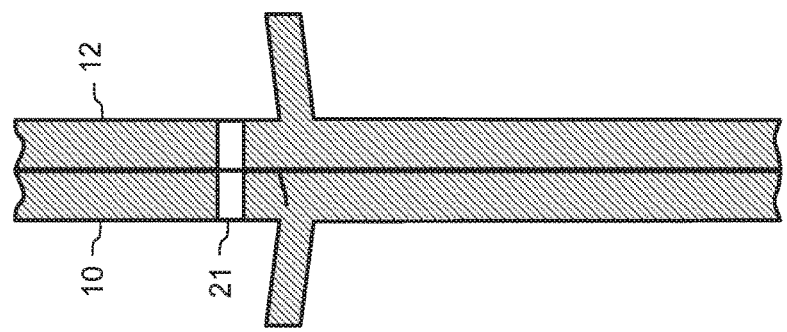
Figure 4A:
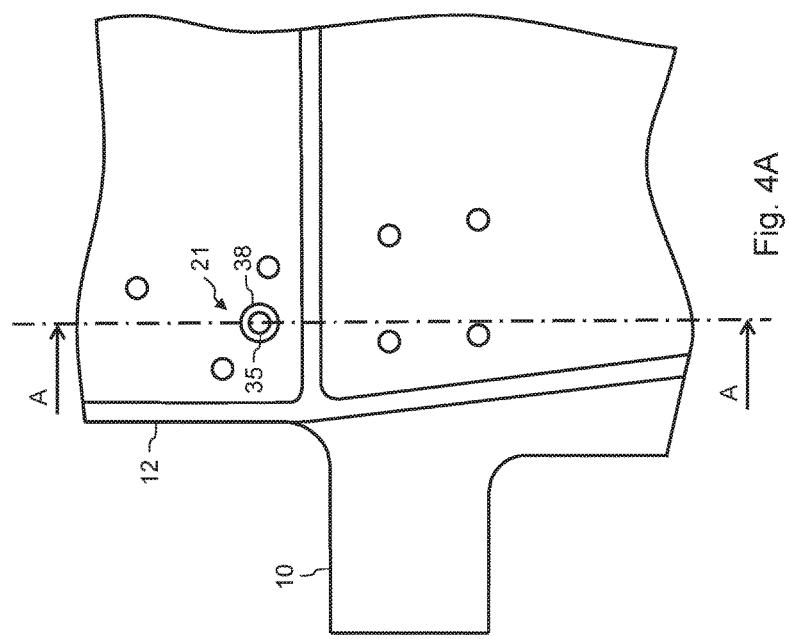
FIGS. 4A and 4B, similar to FIGS. 3A and 3B respectively, represent a structural component into which a probe according to an embodiment of the invention has been inserted.
Figure 4B:
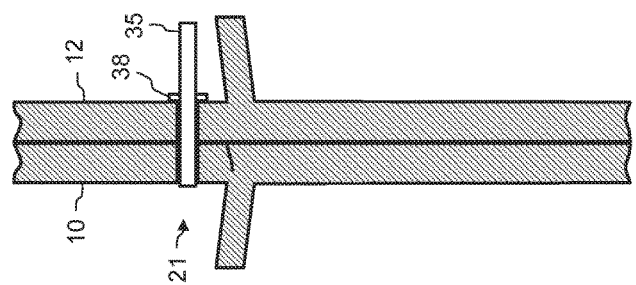

The structural component 10 and the component 12 assembled onto this structural component, shown in FIGS. 4A and 4B, are similar to those described above and shown in FIGS. 3A and 3B. A probe 35 is inserted into the hole 21 which is common to the structural component 10 and the component 12. The probe 35 is equipped with a rotation sensor 38. The probe 35 comprises at least one ultrasonic transducer 36, as shown in FIG. 5B. When its emission is controlled, this ultrasonic transducer emits an ultrasound beam 37 perpendicular to a longitudinal axis of the probe. The probe 35 is positioned so that the ultrasound beam is emitted in the thickness of the structural component 10. Preferably, a commonly used gel is applied to the probe to ensure the transmission of the ultrasound between the probe and the structural component 10 in the hole 21. If this ultrasound beam encounters a discontinuity in the component 10, this beam is reflected in such a way that some of the emitted ultrasound is reflected toward the transducer 36 of the probe. The time interval between the emission of the ultrasound beam and the reception by the probe of an echo corresponding to the reflected ultrasound is characteristic of the distance between the probe and the discontinuity. This discontinuity may, notably, correspond to a crack 15 in the structural component 10. In the example shown in FIGS. 5A and 5B, the probe is oriented in the structural component 10 in such a way that the ultrasound beam is reflected at point B of the crack 15.

Figure 5A:
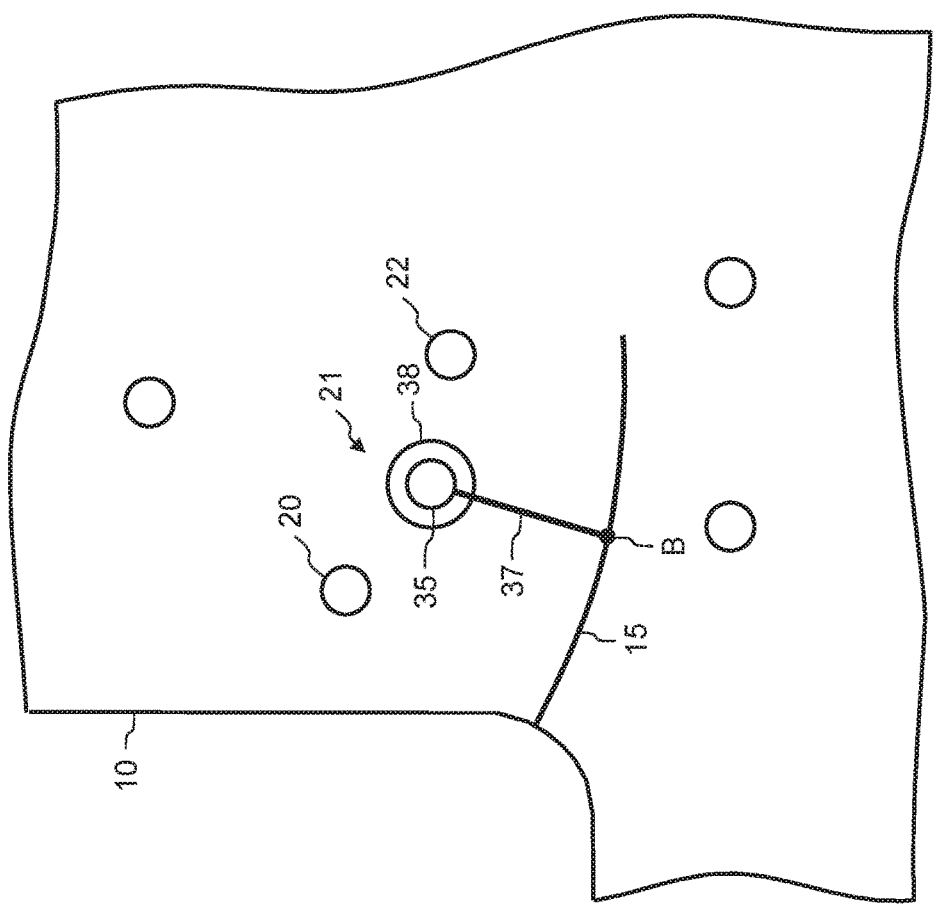
FIGS. 5A and 5B on the one hand, and 5C and 5D on the other hand, show detail views of FIGS. 4A and 4B respectively.
Figure 5B:
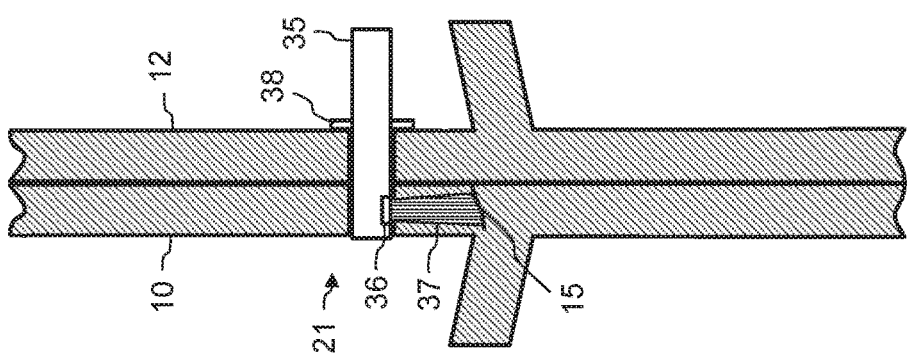
Figure 6:
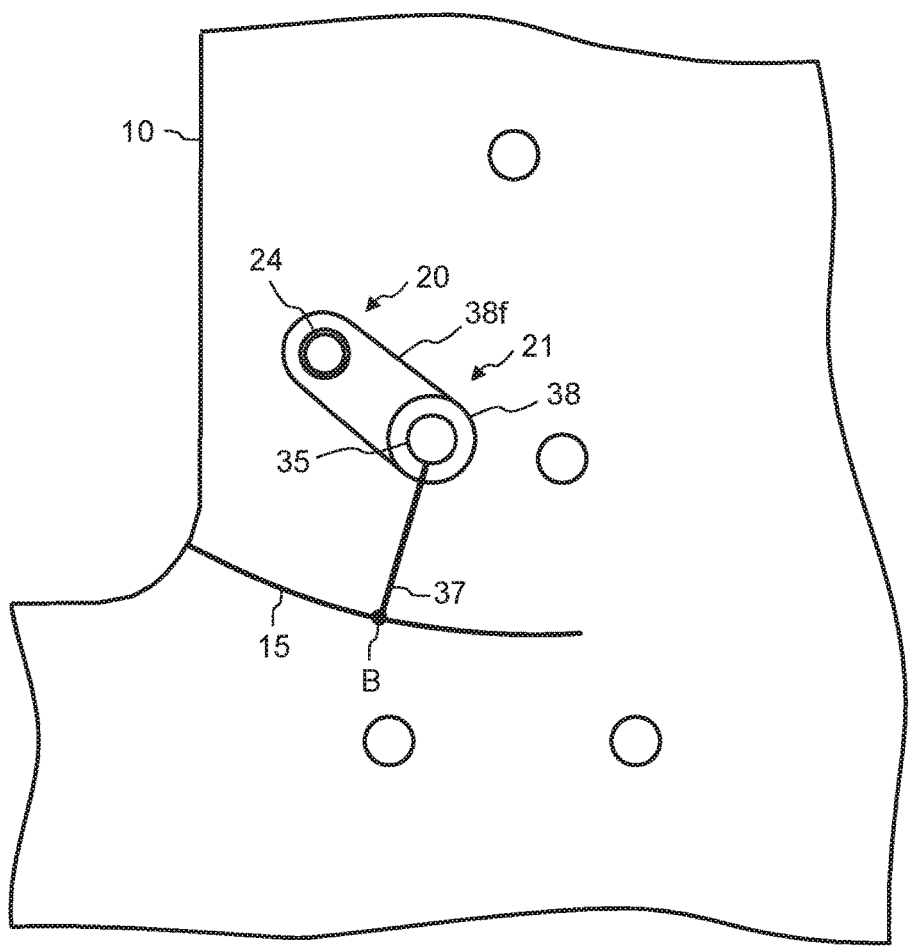
FIGS. 6 and 7 show detail views, similar to that shown in FIG. 5A, illustrating an embodiment of the invention.

When the probe 35 is inserted into the hole 21, an operator positions the rotation sensor 38 in contact with the component 12, as shown in FIGS. 5A and 5B. For the sake of clarity, the component 12 is not shown in FIG. 5A. Advantageously, the rotation sensor is a rotary encoder. It comprises two parts which are rotationally movable relative to one another, namely a first part fixed to the probe 35 and a second part designed to be fixed to the component 12 when the probe 35 is inserted into the hole 21. In one alternative, the rotary encoder is an incremental encoder; in another alternative, it is an absolute encoder. When it is linked to a control system, if the first part and the second part move rotationally relative to one another, the rotation sensor 38 delivers a signal representative of the rotation. Thus the control system determines the current angular position of the probe 35. According to a first variant, a surface of the second part of the rotation sensor 38, designed to be in contact with the component 12 when the probe 35 is inserted into the hole 21, is of a non-slip type. This surface is, for example, coated with a material such as rubber. Thus the operator may move the probe 35 rotationally in the hole 21, while applying a light longitudinal pressure to the probe or to the rotation sensor in the direction of the component 12, without causing the rotation of the second part of the rotation sensor 38: thus this second part remains fixed to the component 12. In a second variant, the rotation sensor 38 comprises a fastening flange 38f fixed to the second part, as shown in FIG. 6. This fastening flange has a hole designed to interact with another hole in the component 12, for example one of the holes 20 or 22. When he positions the rotation sensor 38 on the component 12, the operator causes this hole in the fastening flange 38f to be superimposed on the other hole 20 or 22 in the component 12. In the example shown in the figure, the hole in the fastening flange is superimposed on the hole 20 in the component 12. If the other hole 20 is empty, the operator places an insert 24 into this at least one other hole, to fix the second part of the rotation sensor 38 to the component 12: because of this insert 24, the fastening flange 38f, and consequently the second part of the rotation sensor 38, cannot revolve around the probe 35. The insert 24 is, for example, a clip made of plastic material. If the other hole 20 or 22 already contains an assembly screw or bolt, the insert 24 may be a screw head or a nut on the bolt. The above description relates to the insertion of the probe 35 into the hole 21 from the end of the hole 21 corresponding to the component 12. This procedure is particularly useful if the other end of the hole, corresponding to the structural component 10, is difficult or impossible to access. Without departure from the scope of the invention, if this other end of the hole is accessible, the operator could insert the probe into the hole 21 from this other end corresponding to the structural component 10. He would then place the rotation sensor 38 in contact with the structural component 10.

Figure 10:
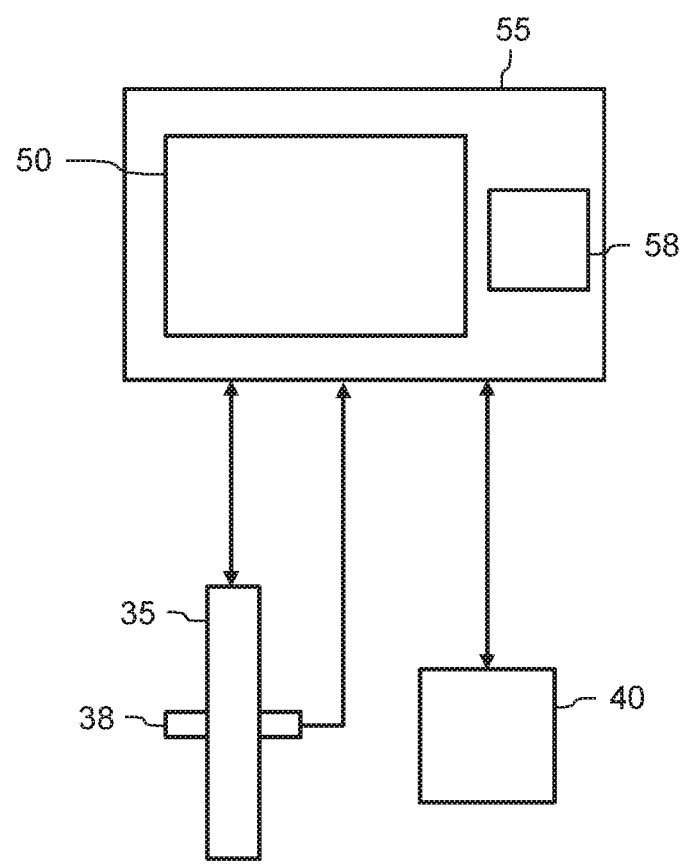
FIG. 10 shows in a schematic manner an example of an automatic control system.

An angular position of the probe 35 in the hole 21 corresponds to a direction of emission of the ultrasound beam 37 that may be emitted by the transducer 36 of the probe. The ultrasound beam shown in FIG. 6 is reflected by the crack 15 at a point B. As mentioned above, the measurement of the reflected ultrasound may be used to determine the distance between the probe and the point B. The point B may thus be characterized by a pair of data elements corresponding, on the one hand, to the angular position of the probe determined by a control system on the basis of a signal received from the rotation sensor 38 and, on the other hand, to the distance measured between the probe and the point B. This pair of data elements forms polar coordinates in a reference frame centered on the point 21. In an exemplary embodiment, the probe 35 is linked to a measuring instrument marketed by the company TESTIA® under the trade name "Smart U32." This measuring instrument controls the emission of the ultrasound beam 37 by the probe, measures the reflected ultrasound, and automatically indicates the distance between the probe and the point B. Advantageously, the control system is incorporated in this measuring instrument. In fact, the measuring instrument has available communication ports, of the USB® type for example, and is based on a Windows® software environment in which special-purpose software can be installed, in addition to the basic measurement functions available in the measuring instrument. An example of a control system 55 based on this measuring instrument is shown in FIG. 10. The control system 55 comprises a processing unit 58, for example a processor or a microprocessor. It also comprises a display screen 50, designed, notably, to display measurements made by means of the measuring instrument. The probe 35 is linked to the control system 55 (the measuring instrument) as indicated above. The rotation sensor 38 is also linked to the control system, if necessary via an adapter which is not shown in the figure, and which is connected to a communication port of the control system. The processing unit comprises a software function for determining the angular position of the probe 35 on the basis of signals received from the rotation sensor 38.

Figure 9:
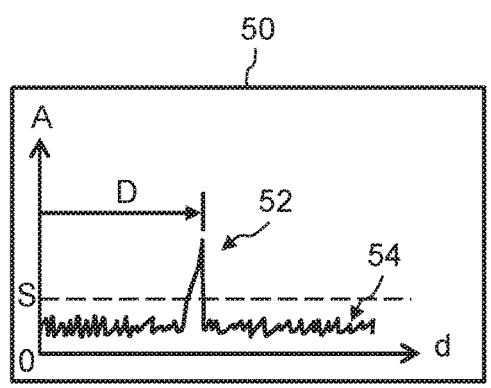
FIG. 9 shows a display on a display screen according to an embodiment of the invention.

In a first embodiment, in order to inspect the crack 15 in the structural component 10, the operator moves the probe 35 rotationally in the hole 21, the probe being linked to the aforementioned measuring instrument 55. This rotational movement of the probe enables the direction of emission of the ultrasound beam by the probe to be varied. If the ultrasound beam is reflected by a discontinuity in the structural component 10, such as the crack 15, the amplitude of the signal supplied by the probe (corresponding to the reflected ultrasound) and measured by the measuring instrument is above a predetermined threshold. FIG. 9 shows an example of a display on the display screen 50 of the measuring instrument. A vertical scale A corresponds to the amplitude of the measured signal, and a horizontal scale d corresponds to the time interval between the emission of the ultrasound beam and the reception of reflected ultrasound. This horizontal scale d therefore corresponds to the distance between the probe and an ultrasound reflection point. A measured signal 54 is displayed on the screen. For distance at which the structural component has no discontinuity, the amplitude of the signal 54 is below a predetermined threshold S. However, for a distance D at which the ultrasound beam is reflected, the signal 54 has a peak amplitude 52 above this predetermined threshold. The display of the peak 52 on the screen enables the operator to read the distance D on the horizontal scale d. If no discontinuity is present in the component in the direction of emission of the ultrasound beam, the signal 54 does not have a peak 52 of this type, and its amplitude is below the predetermined threshold S over the whole of the horizontal scale. When the operator moves the probe rotationally 35 in the hole 21, the direction of emission of the ultrasound beam by the probe varies as mentioned above, and therefore the distance D indicated by the measuring instrument on the screen 50 also varies. In practice, the operator moves the probe 35 rotationally, preferably through a rotation of at least 360°, while monitoring the display on the screen 50. While the operator is moving the probe 35, the control system 55 determines the current angular position of the probe 35 at different instants, by means of the software function of the processing unit 58. Additionally, if the ultrasound beam is reflected at point of discontinuity of the structural component 10, the distance D between the probe and this point of discontinuity is known by the control system 55 and is also displayed on the screen 50. The processing unit 58 of the control system executes software configured to record in a memory pairs of data elements corresponding to the angular position of the probe and the distance D, for a set of points of discontinuity of the structural component 10. In a first variant, the recording of the pairs of data elements corresponds to temporal sampling, coupled to a filtering procedure, so that the pairs of data elements are recorded only if the signal 54 measured and displayed by the measuring instrument has a peak amplitude 52 above the predetermined threshold S, this peak corresponding to a reflection of the ultrasound beam at a point of discontinuity of the structural component 10. Because of this filtering, the pairs of data elements are recorded only if they correspond to points of discontinuity of the structural component 10. In another variant, the recording of the pairs of data elements corresponds to angular sampling (for example, at every 1° of rotation of the probe 35, based on its angular position determined by the control system 55), coupled to a filtering procedure similar to that described for the first variant.

Figure 8:
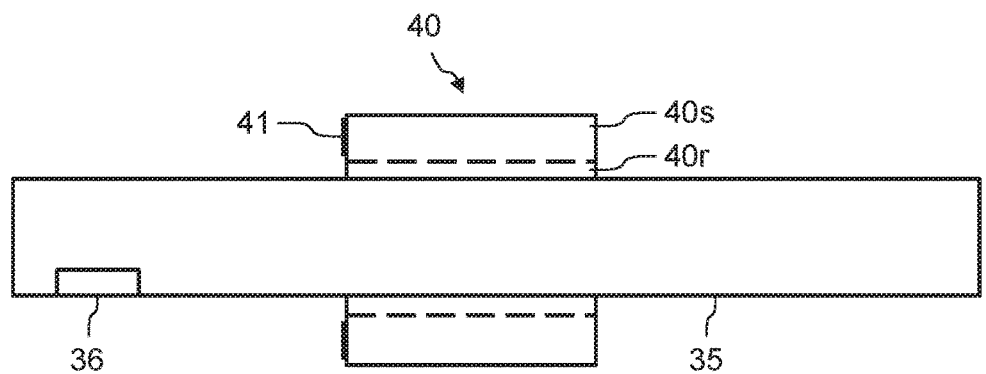
FIG. 8 shows an example of a probe equipped with a motor.

In a second embodiment, the probe 35 is equipped with a motor 40 as shown in FIG. 8. The motor comprises a rotor 40r, fixed to the probe, and a stator 40s. According to a first variant, a surface 41 of the stator 40s, designed to be in contact with the component 12 (or with the structural component 10) when the probe 35 is inserted into the hole 21, is of a non-slip type. This surface is, for example, coated with a material such as rubber. Thus, when the motor is controlled so as to move the probe 35 rotationally in the hole 21, the operator simply has to apply a light longitudinal pressure to the stator in the direction of the component 12 in order to keep the stator fixed to the component 12. In a second variant, the stator 40s comprises a fastening flange, similar to the fastening flange 38f described above for the rotation sensor. This fastening flange enables the stator 40s to be kept fixed to the component 12. The motor 40 is linked to the control system 55 as shown in FIG. 10, if necessary via an adapter (not shown) which is connected to a communication port of the control system. According to a first alternative, the probe 35 is equipped with both the motor 40 and the rotation sensor 38. According to a second alternative, the probe 35 is equipped solely with the motor 40, and the control system 55 determines the angular position of the probe 35 on the basis of the control signals that it sends to the motor. In this second embodiment, after the probe has been placed on the component 12 (or on the structural component 10), the operator does not need to manipulate the probe 35: the rotational movements of the probe are provided by the motor 40 controlled by the control system 55. Thus the control system 55 records pairs of data elements (corresponding to the angular position of the probe and the distance D determined by the control system 55) as in the first embodiment, and its software is also configured to control the rotation of the probe 35 by means of the motor 40.

Figure 7:
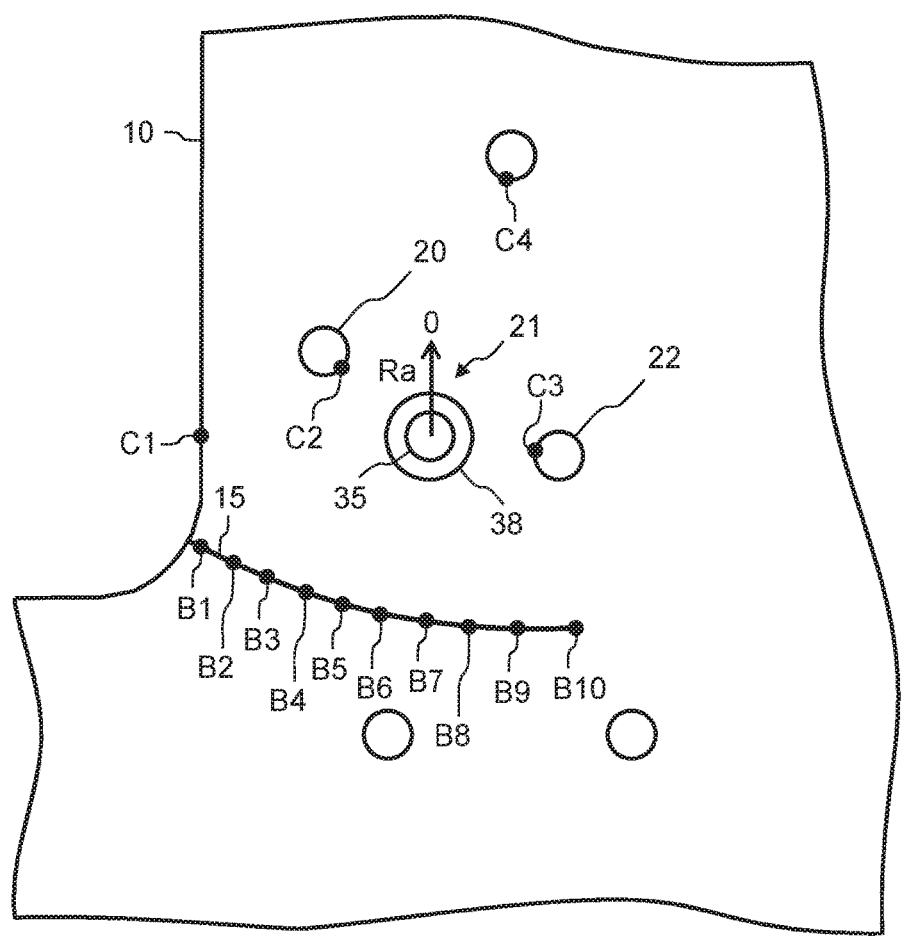

In both the first and the second embodiment, after the recording of the pairs of data elements in the memory, the software of the processing unit 58 executes a function of searching for characteristic points of discontinuity of the structural component 10. These characteristic points of discontinuity correspond to discontinuities of the structural component which are present even in the absence of a crack or defect in the component. They correspond, notably, to edges of the component, to holes pierced in the component, etc. By way of non-limiting example, the points C1, C2, C3 and C4 shown in FIG. 7 correspond to characteristic points of discontinuity of the structural component 10. The coordinates of the characteristic points of discontinuity are known from a plan of the component, for example a digital model of the component. According to a first variant, these coordinates are recorded in a memory of the control system. According to another variant, these coordinates are recorded in a database, and the control system 55 interrogates the database via a data link. If these coordinates are not already expressed in an angular reference frame centered on the hole 21, the software executes a conversion function to find the coordinates of the characteristic points of discontinuity in an angular reference frame of this type centered on the hole 21 and having its orientation determined relative to the structural component 10, for example the angular reference frame Ra shown in FIG. 7, the orientation of which is represented by an arrow corresponding to a direction 0. These coordinates then correspond to polar coordinates, such as the pairs of data elements recorded in the memory by the control system during the rotation of the probe. Regarding these pairs of data elements, the reference frame used is also centered on the hole 21, but is oriented in any direction, since the rotation sensor 38 (or the motor 40) has not undergone an initialization procedure to fix a reference direction relative to the structural component 10. By comparing the coordinates of the characteristic points of discontinuity (expressed in the angular reference frame Ra whose orientation is determined relative to the structural component 10) with the pairs of data elements recorded in the memory, the software searches for the pairs of data elements corresponding to these characteristic points of discontinuity. As a result of this, it calculates a correspondence, in the form of an angular offset, between the angular positions recorded in the pairs of data elements and the angular reference frame Ra linked to the component.

Having determined this correspondence between the recorded angular positions and the angular reference frame linked to the component, the software of the processing unit 58 executes a transformation function based on this correspondence, to transform the pairs of data elements recorded in the memory into polar coordinates expressed in the angular reference frame Ra linked to the component. These polar coordinates define the positions, in the structural component 10, of the points of discontinuity detected during the rotation of the probe 35 in the hole 21.

In a non-limiting specific embodiment of the invention, a new step of measurement acquisition is executed before the execution of the aforementioned transformation function. For this purpose, another rotation of the probe in the hole 21 is performed by the operator, or is controlled automatically by means of the motor 40, and the control system records new pairs of data elements in the memory. The transformation function is then applied to these new pairs of data elements.

Preferably, after the transformation of the pairs of data elements corresponding to the points of discontinuity into polar coordinates expressed in the reference frame linked to the structural component 10, the software executes a filtering function which eliminates all the stored points of discontinuity which correspondent to characteristic points of discontinuity. This makes it possible to retain in memory only the useful data elements corresponding to anomalies detected in the structural component 10, for example the crack 15. In the example shown in FIG. 7, the useful data elements correspond to the coordinates of points B1, B2 . . . B10 located on the crack 15. The software displays these useful data elements on the screen 50 so that the operator can become aware of the anomalies detected in the structural component 10. In one embodiment, the software produces a report containing these useful data elements, which can be exported to a computer to make use of the data elements.

The operator may then, for example, represent the points B1, B2, . . . B10 on a plan of the component, regardless of whether this is a paper plan or a computer plan. The measurement of the distance between one edge of the structural component 10, near the point B1, and the point B10 enables the operator to determine a length of the crack 15 in the structural component 10.

Advantageously, the software of the processing unit 58 further comprises a calculation function configured for automatically calculating the length of the crack 15 on the basis of the useful data elements corresponding to the points B1, B2 . . . B10, in order to display this length on the screen 50 and/or to include it in the report.

In particular, the hole 21 is a hole corresponding to a fastening which is common to the structural component 10 and the component 12. To enable the probe to be inserted into this hole, the operator first removes this fastening, and then puts it back into position when he has finished the inspection of the crack in the structural component.

In an advantageous embodiment, the crack testing method is repeated with the probe 35 inserted into at least two holes in the structural component 10, for example the aforementioned hole 21 and the hole 22 and/or 20. This makes it possible to detect points of reflection of the ultrasound beam 37 from the crack which would not be accessible from the first hole 21, for example points which would be masked by another hole in the component. This embodiment also enables a plurality of measurements to be made of the position of the same point, thereby improving the precision of the position of the crack 15.

Figure 11A:
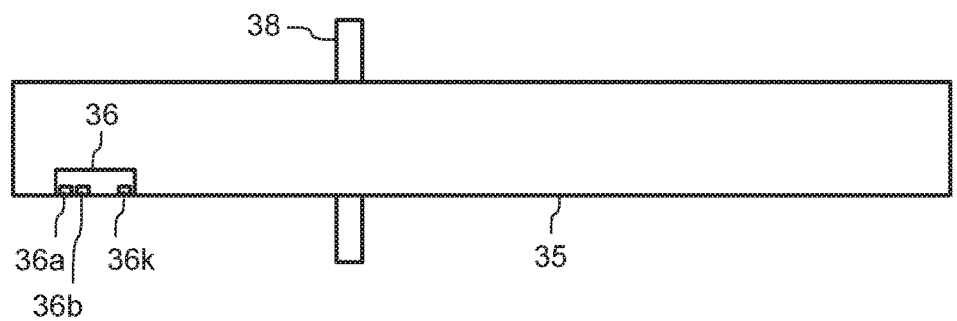
FIG. 11A shows in a simplified manner a multi-element ultrasonic probe.
Figure 11B:
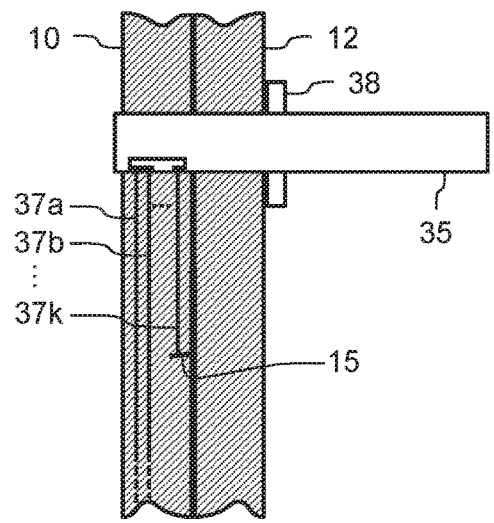
FIG. 11B is a detail view illustrating the use of the probe shown in FIG. 11A, according to an embodiment of the invention.

In an advantageous embodiment, the probe 35 is a multi-element ultrasonic probe (also known as a "phased array" in English), as shown in FIG. 11A. The probe then comprises a sensor 36 which has a plurality of transducers 36a, 36b . . . 36k placed parallel to a longitudinal axis of the probe. Each of the transducers 36a, 36b . . . 36k may emit an ultrasound beam 37a, 37b . . . 37k respectively, as shown in FIG. 11B. Thus, the use of this multi-element probe makes it possible to emit ultrasound beams in various locations distributed through the thickness of the structural component 10, as shown in FIG. 11B. The probe is controlled by the measuring instrument so as to emit the various ultrasound beams successively in time, so that the echoes of the beams do not interfere with one another. The use of a plurality of ultrasound beams enables a finer analysis of the crack 15 to be made. This is, notably, useful if the crack 15 affects only a limited part of the thickness of the component 10, as in the case shown in FIG. 11B: the crack is detected by the ultrasound beam 37k, while it is not detected by the other beams. In particular, instead of controlling the emission of a plurality of beams 37a, 37b . . . 37k successively, the measuring instrument may be configured to control the probe in a mode called the angular scanning mode, making it possible to choose the trajectory of an ultrasound beam emitted into the structural component.

Figure 12A:
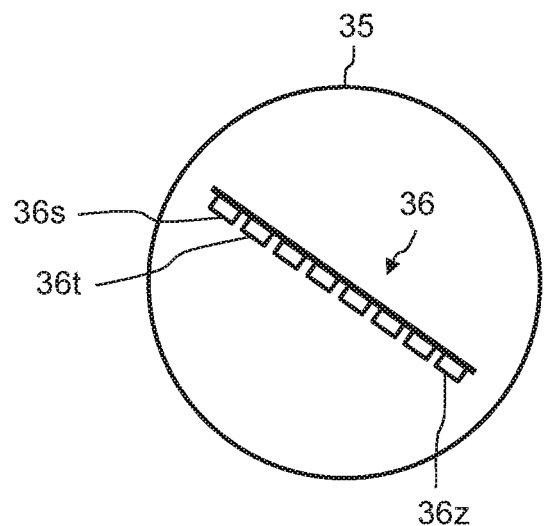
FIG. 12A is a sectional view, in a plane perpendicular to its longitudinal axis, of a multi-element ultrasonic probe.

In a variant shown in FIG. 5C, the probe used is a multi-element probe comprising a sensor 36 as shown in FIG. 5D. Using this multi-element probe enables the structural component to be tested without moving the probe. This sensor 36 comprises a plurality of ultrasonic transducers 36s, 36t . . . 36z, as shown in FIG. 12A. As the sensor 36 comprises a plurality of ultrasonic transducers (8, for example), this sensor is placed inside the probe 35 rather than on its surface, for reasons of integration. The space between the sensor 36 and the surface of the probe is then filled with a material which conducts ultrasound. When it is controlled by a control system, the sensor 36 emits an ultrasound beam 37 perpendicular to a longitudinal axis of the probe. The ultrasound beam is emitted in a direction of emission which is controlled by the control system, according to what is known as an angular scanning method. The probe 35 is positioned so that the ultrasound beam is emitted in the thickness of the structural component 10. Preferably, a commonly used gel is applied to the probe to ensure the transmission of the ultrasound between the probe and the structural component 10 in the hole 21. If this ultrasound beam encounters a discontinuity in the component 10, this beam is reflected in such a way that some of the emitted ultrasound is reflected toward the transducer 36 of the probe. The time interval between the emission of the ultrasound beam and the reception by the probe of an echo corresponding to the reflected ultrasound is characteristic of the distance between the probe and the discontinuity. This discontinuity may, notably, correspond to a crack 15 in the structural component 10. In the example shown in FIG. 5C, the ultrasound beam is emitted in a direction of emission controlled by the control system, in such a way that the ultrasound beam is reflected at point B of the crack 15.

When the probe 35 is inserted into the hole 21, an operator positions the stop 38 against the component 12, as shown in FIGS. 5C and 5D. For the sake of clarity, the component 12 is not shown in FIG. 5C. The stop 38 enables the longitudinal position of the probe 35 relative to the structural component 10 to be secured, so that the ultrasound beam is emitted in the thickness of the structural component 10. The hole 21 may be a hole with a circular cross section, but this is not essential. If the hole does not have a circular cross section (for example, if it is a hole with a rectangular, square or oblong cross section), the cross section of the probe is preferably chosen to be complementary to that of the hole, as a result of which the orientation of the probe relative to the structural component 10 is fixed because of its insertion into the hole. During the manufacture of the probe, the position of the sensor 36 in the probe is then chosen in such a way that the sensor can emit an ultrasound beam in a set of directions that enables the whole of an area of interest 14 to be tested, when the probe is controlled by the control system. If the hole 21 has a circular cross section, the operator orientates the probe 35 in the hole in such a way that the probe can emit an ultrasound beam in a set of directions that enables the whole of an area of interest 14 to be tested, when the probe is controlled by the control system, without any movement of the probe.

As mentioned above, if the probe 35 is connected to a control system, this control system can control the emission of an ultrasound beam by the probe in a direction of emission controlled by the control system, using an angular scanning method. The ultrasound beam 37 shown in FIG. 6 is reflected by the crack 15 at a point B. As mentioned above, the measurement of the reflected ultrasound may be used to determine the distance between the probe and the point B. The point B may thus be characterized by a pair of data elements corresponding, on the one hand, to the direction of emission of the ultrasound beam by the probe 35 (controlled by the control system) and, on the other hand, to the distance determined between the probe and the point B. This pair of data elements forms polar coordinates in a reference frame centered on the point 21. In an exemplary embodiment, the control system to which the probe 35 is linked is a measuring instrument marketed by the company TESTIA® under the trade name "Smart U32." This measuring instrument controls the emission of the ultrasound beam 37 by the probe, measures the reflected ultrasound, and automatically indicates the distance between the probe and the point B.

To test for the crack 15 in the structural component 10, the control system 55 comprises special-purpose software. This special-purpose software, executed by the processing unit 58, is configured to control the emission of an ultrasound beam by the probe 35 in successive directions of emission of a set of directions of emission specified to test the whole of the area of interest 14, without any movement of the probe between the measurements corresponding to the different directions of emission. In an exemplary embodiment, successive directions of emission are spaced apart angularly by an angle of 1°. If the ultrasound beam is reflected by a discontinuity in the structural component 10, such as the crack 15, the amplitude of the signal supplied by the probe (corresponding to the reflected ultrasound) and measured by the measuring instrument 55 is above a predetermined threshold. The software of the control system 55 is configured in such a way that, if this ultrasound beam is reflected by a discontinuity of the structural component 10 in one direction of emission, the software controls the recording in the memory of a pair of data elements corresponding to the direction of emission of the ultrasound beam by the probe and to the distance D determined between the probe and the discontinuity. Thus the software successively records in the memory a set of pairs of data elements, each corresponding to the direction of emission of an ultrasound beam by the probe and to the distance D between the probe and a point of discontinuity corresponding to this direction of emission. These pairs of data elements correspond to the set of points of discontinuity of the structural component 10 detected by the control system 55. The recording of the pairs of data elements by the control system 55 requires no action by operator on the probe after it has been positioned in the hole 21.

After the recording of the pairs of data elements in the memory, the software of the processing unit 58 executes a function of searching for characteristic points of discontinuity of the structural component 10. These characteristic points of discontinuity correspond to discontinuities of the structural component which are present even in the absence of a crack or defect in the component. They correspond, notably, to edges of the component, to holes pierced in the component, etc. By way of non-limiting example, the points C1, C2, C3 and C4 shown in FIG. 7 correspond to characteristic points of discontinuity of the structural component 10. The coordinates of the characteristic points of discontinuity are known from a plan of the component, for example a digital model of the component. According to a first variant, these coordinates are recorded in a memory of the control system. According to another variant, these coordinates are recorded in a database, and the control system 55 interrogates the database via a data link. If these coordinates are not already expressed in an angular reference frame centered on the hole 21, the software executes a conversion function to find the coordinates of the characteristic points of discontinuity in an angular reference frame of this type centered on the hole 21 and having its orientation determined relative to the structural component 10. This reference frame is called the first reference frame in the remainder of the description. The coordinates of the characteristic points of discontinuity then correspond to polar coordinates, such as the pairs of data elements recorded in the memory by the control system. Regarding these pairs of data elements, the reference frame used is also centered on the hole 21. It is called the second reference frame in the remainder of the description. If the position of the probe 35 is fixed relative to the structural component 10 as a result of its insertion into a hole 21 having a non-circular cross section, then, unless there is an error in manipulation or measurement, this second reference frame relating to the pairs of data elements must substantially correspond to the first reference frame. If the hole 21 has a circular cross section, the operator orientates the probe in the hole in such a way that it can emit an ultrasound beam throughout the whole of the area of interest 14. However, in this case the orientation of the probe may be imprecise, and there may be an angular offset between the first reference frame and the second reference frame. When it executes the function of searching for characteristic points of discontinuity, the software compares the coordinates of the characteristic points of discontinuity (expressed in the first reference frame) with the pairs of data elements recorded in the memory (the coordinates expressed in the second reference frame), in order to search for the pairs of data elements corresponding to these characteristic points of discontinuity. As a result of this, it calculates a correspondence, in the form of an angular offset, between the directions of emission recorded in the pairs of data elements (the coordinates expressed in the second reference frame) and the first reference frame. Having determined this correspondence, the software of the processing unit 58 executes a transformation function based on this correspondence, to transform the pairs of data elements recorded in the memory into polar coordinates expressed in the first reference frame linked to the component. These polar coordinates define the positions, in the structural component 10, of the points of discontinuity detected by the control system 55. The function of searching for characteristic points of discontinuity of the structural component 10 and the transformation function are especially useful when the hole 21 has a circular cross section and a template 18 is not used. However, the function of searching for characteristic points of discontinuity may also be useful outside this situation: if there is an error in manipulation or measurement, there is a risk that the function of searching for characteristic points of discontinuity may not find the characteristic points of discontinuity among the pairs of data elements recorded, and the software may then alert the operator to a problem.

Preferably, the software executes a filtering function which eliminates all the points of discontinuity stored in the memory which correspond to characteristic points of discontinuity. This makes it possible to retain in memory only the useful data elements corresponding to anomalies detected in the structural component 10, for example the crack 15. In the example shown in FIG. 7, the useful data elements correspond to the coordinates of points B1, B2 . . . B10 located on the crack 15. The software displays these useful data elements on the screen 50 so that the operator can become aware of the anomalies detected in the structural component 10. In one embodiment, the software produces a report containing these useful data elements, which can be exported to a computer to make use of the data elements.

The operator may then, for example, represent the points B1, B2, . . . B10 on a plan of the component, regardless of whether this is a paper plan or a computer plan. The measurement of the distance between one edge of the structural component 10, near the point B1, and the point B10 enables the operator to determine a length of the crack 15 in the structural component 10.

Advantageously, the software of the processing unit 58 further comprises a calculation function configured for automatically calculating the length of the crack 15 on the basis of the useful data elements corresponding to the points B1, B2 . . . B10, in order to display this length on the screen 50 and/or to include it in the report.

Figure 12B:
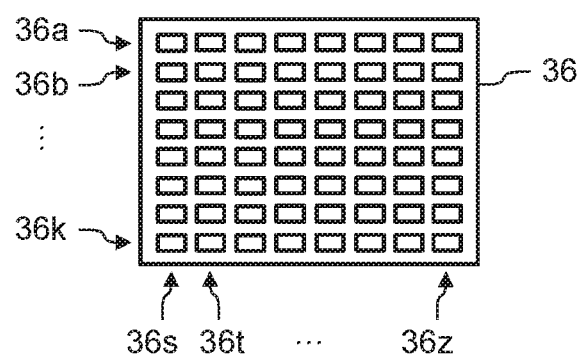
FIG. 12B represents a two-dimensional multi-element ultrasonic probe.

In an advantageous embodiment, the probe 35 is a two-dimensional multi-element ultrasonic probe, that is to say, a probe using a sensor whose ultrasonic transducers are arranged in two dimensions. An example of a sensor 36 of this type of probe is shown in FIG. 12B. The sensor comprises a set of transducers arranged in the form of a matrix in the rows 36a, 36b . . . 36k and columns 36s, 36t . . . 36z. Thus the sensor shown in the figure comprises 64 transducers, arranged in 8 rows and 8 columns. Other arrangements of the transducers are possible without departure from the scope of the invention. The columns of transducers 36s, 36t . . . 36z are placed parallel to a longitudinal axis of the probe. Each row of transducers may be controlled by the control system to emit an ultrasound beam in a direction of emission controlled by the control system, as mentioned above. Each of the rows of transducers 36a, 36b . . . 36k can thus emit an ultrasound beam when controlled by the control system. The use of this multi-element probe makes it possible to emit ultrasound beams in various locations distributed through the thickness of the structural component 10. The probe is controlled by the measuring instrument so as to emit the various ultrasound beams successively in time, so that the echoes of the beams do not interfere with one another. The use of a plurality of ultrasound beams enables a finer analysis of the crack 15 to be made. This is, notably, useful if the crack 15 affects only a limited part of the thickness of the component 10. In particular, instead of controlling the emission of a plurality of beams successively, the measuring instrument may be configured to control the probe in a mode called the angular scanning mode, making it possible to choose the trajectory of an ultrasound beam emitted into the structural component. As the sensor 36 is of a matrix type, the angular scanning is then controlled by the control system in two dimensions.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for crack testing in a structural component of a vehicle, comprises the following steps:
    a) identifying a hole of circular cross section in the structural component and inserting into the hole a probe comprising at least one ultrasonic transducer, the probe being equipped with at least one of a rotation sensor or a motor;
    b) moving the probe rotationally in the hole so as to move the direction of emission of an ultrasound beam by the probe, and, for each angular position of the probe among a set of different angular positions of the probe, performing the following sub-steps automatically, by means of a control system:
        b1) controlling the emission of an ultrasound beam into the structural component;
        b2) measuring a signal supplied by the probe, corresponding to an echo of the emitted ultrasound beam;
        b3) if the amplitude of the measured signal is above a predetermined threshold:
            determining a distance between the probe and a point of discontinuity in the structural component, on the basis of the measured signal;
            determining the angular position of the probe;
            recording a data set comprising at least the distance between the probe and the point of discontinuity, together with a data element corresponding to the angular position of the probe,
    c) by means of the control system:
        automatically searching, among the data sets recorded for the different angular positions of the probe, data sets corresponding to characteristic points of discontinuity of the structural component, the characteristic points of discontinuity corresponding to discontinuities of the structural component which are present even in the absence of a crack or defect in the component; and
        on the basis of data sets corresponding to these characteristic points of discontinuity, establishing a correspondence between the angular positions of the probe on the one hand, and an angular reference frame linked to the component on the other hand;
    d) on the basis of the data sets recorded for the different angular positions of the probe, automatically determining, by means of the control system, the positions in the structural component of the points of discontinuity corresponding to the angular positions of the probe for which the amplitude of the measured signal is above the predetermined threshold;
    e) determining at least one dimensional characteristic of a crack in the structural component on the basis of the positions of said points of discontinuity.

2. The method as claimed in claim 1, wherein the probe being equipped with a motor, in step b) the rotational movement of the probe in the hole is controlled automatically by the control system.

3. The method as claimed in claim 1, wherein the rotation sensor being a rotary encoder, in step a) the probe is inserted into the hole until the rotary encoder comes into contact with the structural component or with a component assembled onto the structural component.

4. The method as claimed in claim 1, wherein the step b) is repeated after step c).

5. The method as claimed in claim 1, wherein step e) is executed automatically by the control system.

6. The method as claimed in claim 5, wherein step e) comprises the determination of a length of the crack in the structural component.

7. The method as claimed in claim 1, wherein, in step a), the probe is inserted into the hole in the structural component through another component adjacent to the structural component.

8. The method as claimed in claim 1, wherein steps a), b), c) and d) are repeated for at least two holes in the structural component.

9. The method as claimed in claim 1, wherein the probe being a multi-element ultrasonic probe, step b) is repeated with the ultrasound beam emitted toward a plurality of locations distributed within the thickness of the structural component.

10. The method as claimed in claim 1, wherein the probe being a multi-element ultrasonic probe, steps b1) to b3) are repeated with the ultrasound beam emitted toward a plurality of locations distributed within the thickness of the structural component.

11. A method for crack testing in a structural component of a vehicle, comprising the following steps:
    a) identifying a hole in the structural component and inserting a multi-element ultrasonic probe into the hole, while orientating the probe according to a region of interest of the structural component, the probe being controllable so as to allow the emission of an ultrasound beam at least in a set of different directions of emission without moving the probe;
    b) without moving the probe, for each direction of emission among the set of different directions of emission of the ultrasound beam, performing the following sub-steps automatically by means of a control system:
        b1) controlling the emission by the probe of an ultrasound beam into the structural component, in the direction of emission;
        b2) measuring a signal supplied by the probe, corresponding to an echo of the emitted ultrasound beam;
        b3) if the amplitude of the measured signal is above a predetermined threshold:
            determining a distance between the probe and a point of discontinuity in the structural component, on the basis of the measured signal;
            recording a data set comprising at least said distance between the probe and the point of discontinuity, together with a data element characterizing the direction of emission of the ultrasound beam, this data set characterizing the position of the detected point of discontinuity,
    c) automatically searching, by means of the control system, among the data sets recorded for the different angular positions of the probe, for data sets corresponding to characteristic points of discontinuity of the structural component, in order to establish a correspondence between the angular positions of the probe on the one hand, and an angular reference frame linked to the component on the other hand, the characteristic points of discontinuity corresponding to discontinuities in the structural component being present even in the absence of any crack or defect in the component;
d) automatically determining, by means of the control system, the positions in the structural component of the points of discontinuity detected in step b), on the basis of the data elements recorded in step b) and the correspondence established in step c) between the angular positions of the probe on the one hand, and an angular reference frame linked to the component on the other hand;
e) determining at least one dimensional characteristic of a crack in the structural component on the basis of the positions of the points of discontinuity.

\* \* \* \* \*